US009505803B2

(12) United States Patent
Frauenschuh et al.

(10) Patent No.: US 9,505,803 B2
(45) Date of Patent: Nov. 29, 2016

(54) WASH SOLUTION AND METHOD FOR AFFINITY CHROMATOGRAPHY

(75) Inventors: Achim Frauenschuh, Werentzhouse (FR); Kurt Bill, Hägendorf (CH)

(73) Assignee: Novartis AG, Basel (CH)

( * ) Notice: Subject to any disclaimer, the term of this patent is extended or adjusted under 35 U.S.C. 154(b) by 488 days.

(21) Appl. No.: 13/516,960

(22) PCT Filed: Dec. 17, 2010

(86) PCT No.: PCT/EP2010/070076
§ 371 (c)(1),
(2), (4) Date: Jul. 12, 2012

(87) PCT Pub. No.: WO2011/073389
PCT Pub. Date: Jun. 23, 2011

(65) Prior Publication Data
US 2012/0283416 A1    Nov. 8, 2012

Related U.S. Application Data

(60) Provisional application No. 61/288,059, filed on Dec. 18, 2009.

(51) Int. Cl.
| A23J 1/00 | (2006.01) |
| C07K 1/00 | (2006.01) |
| C07K 14/00 | (2006.01) |
| C07K 17/00 | (2006.01) |
| C07K 1/22 | (2006.01) |
| C07K 16/00 | (2006.01) |

(52) U.S. Cl.
CPC ........... *C07K 1/22* (2013.01); *C07K 16/00* (2013.01)

(58) Field of Classification Search
None
See application file for complete search history.

(56) References Cited

U.S. PATENT DOCUMENTS

| 5,429,746 | A | 7/1995 | Shadle et al. |
| 6,127,526 | A | 10/2000 | Blank |
| 6,333,398 | B1 | 12/2001 | Blank |
| 6,417,335 | B1 | 7/2002 | Basey et al. |
| 6,620,918 | B2 | 9/2003 | Ansaldi et al. |
| 6,870,034 | B2 | 3/2005 | Breece et al. |
| RE40,070 | E | 2/2008 | Shadle et al. |
| 7,332,289 | B2 | 2/2008 | Takeda et al. |
| 7,714,111 | B2 | 5/2010 | Sun et al. |
| RE41,555 | E | 8/2010 | Shadle et al. |
| RE41,595 | E | 8/2010 | Shandle et al. |
| 7,847,071 | B2 | 12/2010 | Bonnerjea et al. |
| 7,927,815 | B2 | 4/2011 | Takeda et al. |
| 8,084,032 | B2 | 12/2011 | Yumioka et al. |
| 2005/0287210 | A1* | 12/2005 | Ron ............................ 424/468 |
| 2006/0142549 | A1 | 6/2006 | Takeda et al. |
| 2007/0060741 | A1 | 3/2007 | Kelley et al. |
| 2008/0051340 | A1 | 2/2008 | Lu et al. |
| 2008/0064861 | A1 | 3/2008 | Sun |
| 2010/0190210 | A1 | 7/2010 | Arunakumari et al. |
| 2010/0190961 | A1 | 7/2010 | Eon-Duval et al. |
| 2010/0311952 | A1 | 12/2010 | Falkenstein et al. |
| 2011/0040075 | A1 | 2/2011 | Bonnerjea et al. |
| 2011/0105725 | A1 | 5/2011 | Nielsen et al. |
| 2011/0144311 | A1 | 6/2011 | Chmielowski et al. |
| 2012/0142901 | A1 | 6/2012 | Yumioka et al. |

FOREIGN PATENT DOCUMENTS

| EP | 0333474 A2 | 8/1989 |
| EP | 0333474 A2 * | 9/1989 |
| EP | 0746398 B1 | 12/1996 |
| EP | 1084136 B1 | 3/2001 |
| EP | 1380589 A1 | 1/2004 |
| EP | 1561756 A1 | 8/2005 |
| EP | 1568710 A2 | 8/2005 |
| EP | 1601697 B1 | 12/2005 |
| EP | 2261230 A1 | 12/2010 |
| EP | 2336149 A1 | 6/2011 |
| WO | 2007/108955 A1 | 9/2007 |
| WO | 2007143161 A2 | 12/2007 |
| WO | 2008/025748 A1 | 3/2008 |
| WO | 2008/031020 A2 | 3/2008 |
| WO | 2008/087184 A2 | 7/2008 |
| WO | 2008/145351 A1 | 12/2008 |
| WO | 2009/138484 A2 | 11/2009 |
| WO | 2010/019493 A1 | 2/2010 |
| WO | 2011/073389 A1 | 6/2011 |
| WO | 2012/164046 A1 | 12/2012 |

OTHER PUBLICATIONS

Bio-Rad Material Safety Data Sheet for catalog No. 1536161, Protein A MAPS II Binding Buffer, printing date Jul. 25, 2013, pp. 1-7.*
Ritzen, Ulrika et al., "Endotoxin reduction in monoclonal antibody preparations using arginine," Journal of Chromatography B, vol. 856:343-347 (2007).
International Search Report for Application No. PCT/EP2012/060313, 5 pages, dated Jul. 25, 2012.
GE Healthcare Data File 18-1149-94 AE Affinity chromatography: MabSelect, XP055090722, Uppsala Retrieved from the Internet: URL:http://www.gelifesciences.co.jp/catalog/pdf/18114994.pdf.
Protein A Antibody Purification Handbook, XP055090724, Littleton, MA, USA Retrieved from the Internet: URL:http://www.protein-chem.com/Resources/proteus A.3.pdf.
Affi-Prep- Protein A Matrix Instruction Manual LIT-230 Rev B, last modification of PDF file: 1999),XP055090731, Retrieved from the Internet: URL:http://www.bio-rad.com/webroot/web/pdf/lsr/literature/LIT230.pdf.
Arakawa, Tsutomu et al., "Elution of antibodies from a Protein-A column by aqueous arginine solutions," Protein Expression and Purifications, vol. 36:244-248 (2004).
Arakawa, Tsutomu et al., "Suppression of protein interactions by arginine: A proposed mechanism of the arginine effects," Biophysical Chemistry, vol. 127:1-8 (2007).

(Continued)

*Primary Examiner* — Zachary Skelding
*Assistant Examiner* — James Rogers
(74) *Attorney, Agent, or Firm* — Jim Lynch

(57) ABSTRACT

The invention provides a washing method for affinity chromatography in which a wash solution comprising arginine, or an arginine derivative, and a nonbuffering salt, preferably at high pH, greater than 8.0, is effective in removing impurities, such as high molecular weight species and host cell proteins, while also increasing product concentration in the eluate and maintaining a high percent yield of recovered product.

7 Claims, No Drawings

(56) References Cited

OTHER PUBLICATIONS

Arakawa, Tsutomu et al., "The effects of arginine on refolding of aggregated proteins: not facilitate refolding, but suppress aggregation," Biochemical and Biophysical Research Communications, vol. 304:148-152 (2003).
Barron, S. et al., "Improving Purity on Protein A Affinity Chromatography Media through use of an Arginine Intermediate Wash Step," IP.com—Prior Art Database, IPCOM00127319D, 4 pages, (2005).
Das, Utpal et al., "Inhibition of Protein Aggregation: Supramolecular Assemblies of Arginine Hold the Key," PLoS One, vol. 2(11):e1176, pp. 1-9 (2007).
Ejima, Daisuke et al., "Arginine as an effective additive in gel permeation chromatography," Journal of Chromatography A, vol. 1094:49-55 (2005).
Millipore, "Increasing Purity on ProSep-vA Affinity Chromatography Media using an Intermediate Wash Step," retrieved online at http://www.millipore.com/techpublications/tech1/tb1026en00, 4 pages, (2006).
Nakakido, Makoto et al., "Structure-based analysis reveals hydration changes induced by arginine hydrochloride," Biophysical Chemistry, vol. 137:105-109 (2008).
Schneider, Curtiss P. et al., "Investigation of Cosolute-Protein Preferential Interaction Coefficients: New Insights into the Mechanism by Which Arginine Inhibits Aggregation," J. Phys. Chem. B., vol. 113(7):2050-2058 (2009).
Tanaka, Yoshikazu et al., "Structural evidence for guanidine-protein side chain interactions: crystal structure of CutA from *Pyrococcus horikoshii* in 3 M guanidine hydrochloride," Biochemical and Biophysical Research Communications, vol. 323:185-191 (2004).
Tsumoto, Kouhei et al., "Solubilization of active green fluorescent protein from insoluble particles by guanidine and arginine," Biochemical and Biophysical Research Communications, vol. 312:1383-1386 (2003).
Umetsu, Mitsuo et al., "Nondenaturing solubilization of beta2 microglobulin in inclusion bodies by L-arginine," Biochemical and Biophysical Research Communications, vol. 328:189-197 (2005).
International Search Report and Written Opinion for Application No. PCT/EP2010/070076, 10 pages, dated Mar. 11, 2011.
International Preliminary Report on Patentability and Written Opinion for Application No. PCT/EP2010/070076, 6 pages, dated Jun. 19, 2012.
GE Healthcare Data File 18-1149-94 AE Affinity chromatography: MabSelect, XP055090722, Uppsala Retrieved from the Internet: URL:http://www.gelifesciences.co.jp/catalog/pdf/18114994.pdf, 2006.
Protein A Antibody Purification Handbook, XP055090724, Littleton, MA, USA Retrieved from the Internet: URL:http://www.protein-chem.com/Resources/proteus A.3.pdf, Jan. 2005.
Affi-Prep—Protein A Matrix Instruction Manual LIT-230 Rev B, last modification of PDF file: 1999),XP055090731, Retrieved from the Internet: URL:http://www.bio-rad.com/webroot/web/pdf/lsr/literature/LIT230.pdf.
Yumioka R. et al, Protein Expression and Purification (2010) vol. 70, pp. 218-223.

\* cited by examiner

WASH SOLUTION AND METHOD FOR AFFINITY CHROMATOGRAPHY

BACKGROUND OF THE INVENTION

Affinity chromatography allows for the purification of a protein of interest from a mixture of molecules, such as a cellular harvest, based on the preferential binding of the protein of interest to a target in solid phase, such as a gel matrix. This solid phase component typically is formed into a column through which the mixture containing the protein of interest is applied. In this initial step, called the capture step, the protein of interest specifically binds to the target in solid phase whereas other components in the mixture flow through the column. However, certain components within the mixture, including high molecular weight species (HMWs), low molecular weight species (LMWs) and host cell proteins (HCPs), may remain within the column as impurities along with the protein of interest. Thus, typically one or more wash steps are carried out in which one or more wash solutions are applied to the column to remove these impurities while maintaining the binding of the protein of interest to the solid phase. Finally, after removal of impurities by the washing step(s), the protein of interest is recovered from the column by an elution step, in which an elution solution that disrupts the binding of the protein of interest to the solid phase target, is applied to the column and the protein of interest is recovered in the eluate. Accordingly, the effectiveness of affinity chromatography in purifying a protein of interest depends in large part on identifying wash conditions that allow for efficient removal of impurities (e.g., HMWs, LMWs, HCPs) while not disrupting the binding of the protein of interest to the solid phase target or otherwise having undesired effects.

A particularly useful type of affinity chromatography is Protein A chromatography for the purification of proteins that contain an immunoglobulin Fc region, such as antibodies and Fc fusion proteins. Various wash solutions have been described for removal of impurities from Protein A columns, including wash solutions containing one of the following: hydrophobic electrolytes (e.g., tetramethylammonium chloride, tetraethylammonium chloride, tetrapropylammonium chloride or tetrabutylammonium chloride at pH1-5.0-7.0), solvents (e.g., 5-20% isopropanol or polypropylene/hexylene glycol), urea (e.g., at a concentration of 1-4 M), detergents (e.g., 0.1-1% Tween 20 or Tween 80), polymers (e.g., 5-15% polyethylene glycol such as PEG400 or PEG8000) or highly concentrated buffer solutions such as Tris, HCl, acetate, sulfate, phosphate or citrate buffers at a concentration of 0.8-2.0 M at a pH between 5.0 and 7.0 (see e.g., Shukla, A. A. and Hinckley, P. (2005) *Biotechnol. Prog.* 24:1115-1121; U.S. Pat. Nos. 6,127,526 and 6,333,398 by Blank; and U.S. Pat. No. 6,870,034 by Breece et al.). Many of these chemicals, however, have one or more disadvantages, including but not limited to toxicity, corrosiveness, flammability, instability, costly disposal as hazardous waste and/or inefficient removal of contaminants during the washing step.

Protein A chromatography wash buffers containing salt (such as sodium chloride), alone or in combination with either a detergent (e.g. Tween 20), a solvent (e.g., hexylene glycol) or a polymer (e.g., polyethylene glycol), have also been described (U.S. Pat. No. 6,870,034 by Breece et al.).

Barron et al. describe an intermediate wash solution for Protein A chromatography containing 0.5 to 2.0 M arginine in a phosphate/acetate buffer at pH 5.0-7.5 (optimally 1M arginine, 0.1M phosphate/acetate buffer at pH 5.0). This arginine wash step is reported to remove HCP contaminants. The authors also tested an intermediate wash solution that contained sodium chloride at 0.5-2.0 M at pH 5.0-7.5 but reported that the NaCl wash showed no significant decrease in HCP (Barron et al., "Improving Purity on Protein A Affinity Media Through Use of an Arginine Intermediate Wash Step", http://www.priorartdatabase.com/IPCOM/000127319).

Sun et al. also describe washing of affinity chromatography columns, such as a Protein A column, with a wash buffer that contains arginine, or an arginine derivative, at a concentration of 0.1-2.0 M and at a pH of 4.5-8.0 (U.S. Patent Publication Nos. 20080064860 and 20080064861; PCT Publication No. WO 2008/031020).

Arginine has also been used to elute proteins from affinity chromatography columns and other types of purification columns. For example, Arakawa et al. describe methods of eluting antibodies from a Protein A column using an elution buffer containing 0.5-20 M arginine at pH 4.1-5.0 (Arakawa et al. (2004) *Protein Expression and Purification* 36:244-248; Tsumoto, K, et al. (2004) *Biotechnol. Prog.* 20:1301-1308; U.S. Patent Publication No. 20050176109). Additionally. U.S. Pat. No. 7,501,495 by Ejima et al. describes methods of eluting proteins from a gel filtration column by using a developing solution containing arginine hydrochloride. Ghose et al. describe methods of eluting proteins of interest from underivatized silica using an arginine gradient as the eluant (Ghose, S. et al. (2004) *Biotech. Bioeng.* 87:413-423). U.S. Patent Publication No. 20030050450 by Coffman et al. describes methods of dissociating Fc containing molecules from complexes of the Fe containing molecule and Protein A, wherein the Fc/Protein A complexes are applied to a hydrophobic interaction column (HIC) and the column is washed with a buffer containing arginine.

SUMMARY OF THE INVENTION

This invention provides an efficient and robust wash solution for affinity chromatography, as well as washing methods using this solution. This wash solution is applied in a washing step prior to the elution step, and its use results in high yields and high concentrations of the protein of interest eluted from the affinity matrix while effectively removing both high molecular weight species (HMWs) and host cell proteins (HCPs) from the starting material applied to the matrix. This wash solution is characterized by the presence of both arginine (or an arginine derivative) and a nonbuffering salt, such as a halogen salt. Preferably, the wash solution is at high pH, above 8.0. This combination of arginine (or an arginine derivative) and a nonbuffering salt removes considerably more impurities than wash solutions containing either arginine or salt alone and results in a sharper elution peak correlating with a high concentration of the recovered protein of interest.

Accordingly, in one aspect, the invention provides a method of producing a purified protein of interest using an affinity chromatography (AC) matrix to which a protein of interest is bound, the method comprising washing the AC matrix with one or more wash solutions comprising (i) arginine, or an arginine derivative, and (ii) a nonbuffering salt, prior to elution of the protein of interest from the AC matrix. Preferably, the protein of interest is loaded onto the AC matrix prior to washing with the one or more wash solutions and the protein of interest is eluted from the AC matrix after washing with the one or more wash solutions, in particular, to remove impurities from the AC matrix.

In a preferred embodiment, the AC matrix is a Protein A column. In various other embodiments, the AC matrix can be, for example, selected from the group consisting of a Protein G column, a Protein A/G column, a Protein L column, an immobilized metal ion affinity chromatography (IMAC) column, a calmodulin resin column, a MEP Hyper-Cel™ column, a column that binds maltose binding protein (MBP), a column that binds glutathione-S-transferase (GST) and a column that binds Strep-Tag II. In a preferred embodiment, the protein of interest is an antibody or antibody fragment that binds to the AC matrix, such as a Protein A column, although other proteins that bind to the affinity matrices described herein are also suitable for purification according to the methods of the invention.

In a preferred embodiment, the one or more wash solutions comprise Arginine-HCl, preferably at a concentration in a range of 0.05-2.0 M, more preferably in a range of 0.05-0.85 M, most preferably in a range of 0.1-0.5 M. In particular embodiments, Arginine-HCl is present at a concentration of 0.1 M or about 0.1 M, 0.25 M or about 0.25 M, or 0.5 M or about 0.5 M. In other embodiments, the one or more wash solutions comprise an arginine derivative, such as a derivative selected from the group consisting of acetyl arginine, N-alpha-butyroyl-arginine, agmatine, arginic acid and N-alpha-pyvaloyl arginine. Preferably, the arginine or arginine derivative comprises L-arginine, although D-arginine is also encompassed.

In a preferred embodiment, the nonbuffering salt in the one or more wash solutions is sodium chloride (NaCl), preferably at a concentration in a range of 0.1-2.0 M. In particular embodiments, NaCl is present at a concentration of 0.75 M or about 0.75 M, 1.0 M or about 1.0 M, or 1.25 M or about 1.25 M. In other embodiments, the nonbuffering salt in the one or more wash solutions is selected from the group consisting of potassium chloride, calcium chloride and magnesium chloride.

In a particular embodiment, the pH of the one or more wash solutions is greater than 8.0, preferably at least 8.1, more preferably at least 8.5 and even more preferably at least 8.9. In one embodiment, the pH of the one or more wash solutions is in a range of 8.1-9.5. In another embodiment, the pH of the one or more wash solutions is in a range of 8.5-9.5. In another embodiment, the pH of the one or more wash solutions is about 9.0. In another embodiment, the pH of the one or more wash solutions is 9.0.

The arginine and nonbuffering salt wash combination described herein preferably is applied in a single wash solution that contains both components (i.e., the AC matrix is washed with one wash solution that comprises both (i) arginine or an arginine derivative; and (ii) a nonbuffering salt). Alternatively, two wash solutions, one containing arginine or an arginine derivative (preferably at a pH greater than 8.0) and the other containing a nonbuffering salt can be used in tandem washes. Accordingly, in another embodiment of the washing method, the AC matrix is washed with two wash solutions, a first wash solution and a second wash solution. In one embodiment, the first wash solution comprises arginine, or an arginine derivative, and the second wash solution comprises a nonbuffering salt. In another embodiment, the first wash solution comprises a nonbuffering salt and the second wash solution comprises arginine or an arginine derivative.

The washing method of the invention is effective in removing a variety of impurities, including high molecular weight (HMW) species and host cell proteins (HCPs).

In another aspect, the invention provides a method of producing a purified antibody, or antibody fragment, using a Protein A column, the method comprising (a) loading a mixture comprising the antibody, or antibody fragment, onto the Protein A column; (b) washing the Protein A column with a wash solution comprising (i) Arginine-HCl, at a concentration in a range of 0.05-2.0 M (more preferably 0.05-0.85 M, most preferably 0.1-0.5 M), and sodium chloride, at a concentration in a range of 0.1-2.0 M, wherein the wash solution removes impurities from the Protein A column; and (c) eluting the antibody, or antibody fragment, from the Protein A column. In particular embodiments, Arginine-HCl is present at a concentration of 0.1 M or about 0.1 M, 0.25 M or about 0.25 M, or 0.5 M or about 0.5 M. In particular embodiments, NaCl is present at a concentration of 0.75 M or about 0.75 M, 1.0 M or about 1.0 M, or 1.25 M or about 1.25 M. In various embodiments, the pH of the wash solution is greater than 8.0, preferably at least 8.1, more preferably at least 8.5, more preferably 9.0, in a range of 8.1-9.5, or in a range of 8.5-9.5.

DETAILED DESCRIPTION OF THE INVENTION

The invention provides a new washing solution for affinity chromatography, such as Protein A chromatography, which is applied to the column prior to elution of the protein of interest to remove impurities. The new washing solution is composed of arginine, or an arginine derivative, and a nonbuffering salt. Typically, the washing solution is an aqueous solution.

As used herein, the term "nonbuffering salt" refers to a salt that is present in the wash solution that is of a type, and at a concentration, such that it does not substantially contribute to retaining the pH of the wash solution(s) under the applied conditions (such as high pH) upon addition of acid or base. Typically, the nonbuffering salt is an ionic salt. Nonbuffering salts include halogen salts, including those that comprise Cl or Br (more preferably Cl), in particular halogen salts comprising alkali metals or alkaline earth metals, including Na, K, Ca and Mg (more preferably Na or K). The term "nonbuffering salt" does not include buffering salts, such as sodium acetate, sodium phosphate and Tris, that do substantially contribute to retaining the pH of a wash solution(s) under the applied conditions. In a preferred embodiment, the nonbuffering salt is a halogen salt (e.g., comprising Cl or Br). In another embodiment, the nonbuffering salt is a halogen salt that comprises sodium (Na), potassium (K), calcium (Ca) or magnesium (Mg), more preferably, sodium (Na) or potassium (K). In yet another embodiment, the nonbuffering salt is selected from the group consisting of NaCl, KCl, $CaCl_2$ and $MgCl_2$. In a particularly preferred embodiment, the nonbuffering salt is sodium chloride (NaCl). Typically, the nonbuffering salt is used at a "high" concentration of at least 1 M. Other suitable concentrations and concentration ranges are described further below.

This new combination of wash components removes considerably more impurities than commonly used procedures without affecting recovery. In addition, this washing condition results in a sharper elution peak correlating with a higher concentration of the protein of interest in the eluate, which is advantageous to increase the performance of additional downstream purification processes.

Efficient removal of impurities, including host cell proteins (HCPs) and product-related impurities such as high molecular weight (HMW) species and low molecular weight (LMW) species, is a crucial factor during downstream processing of a protein of interest. Affinity chromatography is often used as the first stage of a multi-stage purification process for a protein of interest (e.g., an antibody) and the purity of the protein of interest after affinity chromatography notably influences the kind and number of subsequent purification steps. Another important role for affinity chromatography is to concentrate the product, which allows for the use of proportionally smaller, less costly columns in subsequent purification steps. Therefore, it is particularly important to optimize the removal of impurities during the affinity chromatography step.

Low pH conditions, typically between pH 3-4, are a requisite to elute the bound protein of interest from the affinity matrix and have the drawback of potentially inducing aggregation. Historically, less stringent conditions, such as pH 5-5.5, have been used to wash nonspecifically bound impurities from the column whilst preserving the interaction between the protein of interest and the affinity matrix. Recovery of the protein of interest, however, is often decreased due to partial elution of the protein of interest at these conditions, especially when working at high loading densities. Accordingly, in a preferred embodiment, the wash solution provided by the present invention is advantageously performed at a high pH, greater than 8.0, which preserves binding of the protein of interest to the affinity matrix while allowing for removal of impurities.

The new wash solution for affinity chromatography provided by the present invention is based on a mixture of arginine (or arginine derivative) and a nonbuffering salt, preferably performed at a high pH. The large biophysical diversity of impurities present in common harvests or cellular extracts results in very diverse modes of interactions with the solid phase of the chromatography medium and/or the bound protein of interest. More or less strong tethering of impurities may be the result of non-covalent intermolecular interactions between the two molecules, such as hydrogen bonding, electrostatic interactions, hydrophobic and Van der Waals forces or a combination of these types of interactions. Therefore, a combination of several different mechanisms to remove impurities is likely to be much more effective than an approach based on a single mechanism for removing impurities.

With respect to the effects of the nonbuffering salt in the wash solution, based on the analytical data herein, high affinity interactions between the protein of interest and ligand of the affinity matrix are not broken by a wash at high nonbuffering salt concentrations, whereas charged contaminants tethered nonspecifically to charged residues on either the immobilized ligand or the bound protein of interest are removed efficiently. Accordingly, while not intending to be limited by mechanism, it is thought that the nonbuffering salt used in the wash solution has the capacity to break ionic interactions between charged contaminants (impurities) tethered nonspecifically to charged residues on one or more components of the affinity chromatography matrix (e.g., the chemical support of the matrix such as a resin, the affinity ligand immobilized on the matrix and/or the target of interest bound to the ligand immobilized on the matrix), while not disrupting the specific binding of the bound target to the immobilized ligand.

With respect to the effects of arginine in the wash solution, it has been reported that arginine is able to solubilize certain precipitated proteins (Umetsu, M. et al. (2005) *Biochem. Biophys. Res. Commun.* 328:189-197; Tsumoto, K. et al. (2003) *Biochem. Biophys. Res. Commun.* 312:1383-1386), reduce the formation of aggregates (Arakawa, T. et al. (2003) *Biochem. Biophys. Res. Commun.* 304:148-152), and reduce nonspecific adsorption of proteins to surfaces (Ejima, D. et al. (2005) *J. Chromatogr. A.* 1094:49-55). While not intending to be limited by mechanism, the reduction of protein aggregation may originate from the masking of hydrophobic patches on the proteins, which interact with arginine. This interaction may take place between the guanidium group on arginine and tryptophan groups on proteins, or through the formation of a hydrophobic patch by clustering of arginine, or may be a combination of such effects.

With respect to the use of a pH greater than 8.0 in the wash solution, a basic pH may partially denature HCPs and HMWs, whereas stable proteins including monomeric antibodies are not influenced at these conditions. While not intending to be limited by mechanism, denaturing of contaminant proteins may be manifested as a slight change in structure, which may be sufficient to weaken nonspecific binding. Therefore, the high pH of the wash solution may be beneficial for increasing the removal of impurities by destabilizing their interaction with the bound protein of interest or the solid support of the affinity matrix.

Accordingly, in one aspect, the invention provide a method of producing a purified protein using an affinity chromatography (AC) matrix to which a protein of interest is bound, the method comprising washing the AC matrix with one or more wash solutions comprising (i) arginine, or an arginine derivative, and (ii) a nonbuffering salt, prior to elution of the protein of interest from the AC matrix.

As used herein, the term "affinity chromatography matrix" or "AC matrix", is intended to refer to a solid phase medium, typically a gel or resin, that allows for separation of biochemical mixtures based on a highly specific binding interaction between a protein of interest and the AC matrix, such as between a receptor and ligand, enzyme and substrate or antigen and antibody. Thus, the solid phase medium comprises a target to which the protein of interest is capable of reversibly affixing, depending upon the buffer conditions. Non-limiting examples of immobilized or solid phase media that can comprise the AC matrix include a gel matrix, such as agarose beads (such as commercially available Sepharose matrices), and a glass matrix, such as porous glass beads (such as commercially available ProSep matrices).

Binding of the protein of interest to the AC matrix typically is achieved by column chromatography. That is, the AC matrix is formed into a column, a biochemical mixture containing a protein of interest is flowed through the column, followed by washing of the column by flowing through the column one or more wash solutions, followed by elution of the protein of interest from the column by flowing through the column an elution buffer.

Alternatively, binding of the protein of interest to the AC matrix can be achieved by batch treatment, in which the biochemical mixtures containing the protein of interest is incubated with the AC matrix in a vessel to allow for binding of the protein of interest to the AC matrix, the solid phase medium is removed from the vessel (e.g., by centrifugation), the solid phase medium is washed to remove impurities and again recovered (e.g., by centrifugation) and the protein of interest is eluted from the solid phase medium.

In yet another embodiment, a combination of batch treatment and column chromatography can be used. For example, the initial binding of the protein of interest to the AC matrix can be achieved by batch treatment and then the solid phase medium can be packed into a column, following by washing of the column and elution of the protein of interest from the column.

The nature of a particular solid phase matrix, in particular the binding properties of the target attached to the solid phase, determines the type(s) of protein(s) that can be purified using that solid phase matrix. For example, in a preferred embodiment of the invention, the AC matrix is a Protein A column, which comprises as the target attached to the solid phase a bacterial cell wall protein, Protein A, that specifically binds the $CH_2$ and $CH_3$ domains within the Fc region of certain immunoglobulins. The binding properties of Protein A are well established in the art. Accordingly, in a preferred embodiment of the invention, the protein of interest (to be purified) is an antibody or antibody fragment comprising an Fc region. Furthermore, additional proteins that can be purified using Protein A chromatography include Fc fusion proteins. Insofar as any protein is capable of specifically binding to a Protein A matrix, it can be purified according to the methods of the invention.

Various Protein A resins are well known in the art and suitable for use in the invention. Non-limiting examples of commercially available Protein A resins include MabSelect, MabSelect Xtra, MabSelect Sure, rProtein A Sepharose FF, rmpProtein A Sepharose FF, Protein A Sepharose CL-4B and nProtein A Sepharose 4 FF (all commercially available from GE Healthcare); ProSep A, ProSep-vA High Capacity, ProSep-vA Ultra and ProSep-Va Ultra Plus (all commercially available from Millipore); Poros A and Mabcapture A (both commercially available from Poros); IPA-300, IPA-400 and IPA-500 (all commercially available from RepliGen Corp.); Affigel protein A and Affiprep protein A (both commercially available from Bio-Rad); MABsorbent A1P and MABsorbent A2P (both commercially available from Affinity Chromatography Ltd.); Protein A Ceramic Hyper D F (commercially available from Pall Corporation); Ultralink Immobilized protein A and Agarose protein A (both commercially available from PIERCE) and Protein A Cellthru 300 and Protein A Ultraflow (both commercially available from Sterogen Bioseparations).

In addition to Protein A chromatography, the washing method of the invention can be applied to other affinity chromatography systems. For example, in another embodiment, the AC matrix can be a Protein G column, a Protein A/G column or a Protein L column, each of which are also immunoglobulin-binding bacterial proteins with binding properties established in the art. Thus, an AC matrix that is a Protein G matrix, a Protein A/G matrix or a Protein L matrix can be used to purify antibodies, antibody fragments comprising an Fc region and Fc fusion proteins.

Other non-limiting examples of AC matrices, and the types of proteins that they are effective in purifying include the following: an immobilized metal ion affinity chromatography (IMAC) column (for purification of proteins with an affinity for metal ions, such as histidine-tagged proteins), a calmodulin resin column (for purification of proteins tagged with calmodulin binding peptide (CBP)), a MEP HyperCel™ column (a cellulose matrix that selectively binds immunoglobulin), a column that binds maltose binding protein (MBP) (such as a Dextrin Sepharose™ resin that selectively binds proteins tagged with MBP), a column that binds glutathione-S-transferase (GST) (such as a Glutathione Sepharose™ resin that selectively binds proteins tagged with GST) and a column that binds Strep-Tag II (such as a Strep-Tactin™ Sepharose resin that selectively binds proteins tagged with Strep-Tag II). Furthermore, immunoaffinity matrices, which comprise an antibody as the target affixed to the solid phase, can be used to purify, an antigen of interest that specifically binds to the antibody affixed to the solid phase.

While the invention of interest is described herein in particular with respect to purification of antibodies using Protein A chromatography, insofar as any protein is known the art to selectively bind to a particular AC matrix, the protein is amenable to purification using the washing methods described herein.

The wash solutions of the invention comprise arginine or an arginine derivative. The arginine which can be used in the present invention may be the natural amino acid arginine (e.g., L-arginine), D-arginine or an arginine derivative. Non-limiting examples of arginine derivatives include acylated arginine, such as acetyl arginine and N-alpha-butyroyl-arginine, agmatine, arginic acid and N-alpha-pyvaloyl arginine. The arginine or arginine derivative can be used in the form of an acid addition salt. Examples of the acid which can form an acid addition salt include hydrochloric acid and the like.

The concentration of arginine or arginine derivative in the wash solution typically is between 0.05 M and 2.0 M (e.g., 0.05 M, 0.1 M, 0.15 M, 0.2 M, 0.25 M, 0.3 M, 0.35 M, 0.4 M, 0.45 M, 0.5 M, 0.55 M, 0.6 M, 0.65 M, 0.7 M, 0.75 M, 0.8 M, 0.85 M, 0.9 M, 0.95 M, 1.0 M, 1.1 M, 1.15 M, 1.20 M, 1.25 M, 1.30 M, 1.35 M, 1.40 M, 1.45 M, 1.5 M, 1.55 M, 1.6 M, 1.65 M, 1.7 M, 1.75 M, 1.8 M, 1.85 M, 1.9 M, 1.95 M, or 2.0 M), more preferably between 0.05 and 0.85 M (which is the upper solubility of arginine in water at 20° C.) (e.g., 0.05 M, 0.1 M, 0.15 M, 0.2 M, 0.25 M, 0.3 M, 0.35 M, 0.4 M, 0.45 M, 0.5 M, 0.55 M, 0.6 M, 0.65 M, 0.7 M, 0.75 M, 0.8 M or 0.85 M), most preferably between 0.1 and 0.5 M (e.g., 0.1 M, 0.15 M, 0.2 M, 0.25 M, 0.3 M, 0.35 M, 0.4 M, 0.45 M, or 0.5 M). In various embodiments, the concentration of arginine or arginine derivative can be, for example, 0.05 M, 0.1 M, 0.2M, 0.25M, 0.3M, 0.4 M, 0.5 M, 0.6 M, 0.7M or 0.8M, or between 0.1 M, and 0.5 M. In certain embodiments, the concentration of arginine or arginine derivative in the wash solution is 0.25 M or greater. In particular embodiments, Arginine is present at a concentration of 0.1 M or about 0.1 M, 0.25 M or about 0.25 M, or 0.5 M or about 0.5 M.

The wash solutions of the invention also comprise a nonbuffering salt, as described above, which is of a type and at a concentration sufficient to break ionic interactions between impurities and one or more components of the affinity matrix. In a preferred embodiment, the nonbuffering salt is a halogen salt. In a particularly preferred embodiment, the nonbuffering salt is sodium chloride (NaCl). In other embodiments, the nonbuffering salt can be, for example, potassium chloride (KCl), calcium chloride ($CaCl_2$) or magnesium chloride ($MgCl_2$). The concentration of nonbuffering salt in the wash solution typically is between 0.1 M and 2.0 M (e.g., 0.1 M, 0.15 M, 0.2 M, 0.25 M, 0.3 M, 0.35 M, 0.4 M, 0.45 M, 0.5 M, 0.55 M, 0.6 M, 0.65 M, 0.7 M 0.75 M, 0.8 M, 0.85 M, 0.9 M, 0.95 M, 1.0 M, 1.1 M, 1.15 M, 1.20 M, 1.25 M, 1.30 M, 1.35 M, 1.40 M, 1.45 M, 1.5 M, 1.55 M, 1.6 M, 1.65 M, 1.7 M, 1.75 M, 1.8 M, 1.85 M, 1.9 M, 1.95 M, or 2.0 M), or between 0.5 M and 1.5 M (e.g., 0.5 M, 0.55 M, 0.6 M, 0.65 M, 0.7 M, 0.75 M, 0.8 M, 0.85 M, 0.9 M, 0.95 M, 1.0 M, 1.1 M, 1.15 M, 1.2 M, 1.25 M, 1.3 M, 1.35 M, 1.4 M, 1.45 M, or 1.5 M), or between 1 M and 2 M (e.g., 1 M, 1.1 M, 1.15 M, 1.2 M, 1.25 M, 1.3 M, 1.35 M, 1.4 M, 1.45 M, 1.5 M 1.55 M, 1.6 M, 1.65 M, 1.7 M, 1.75 M, 1.8 M, 1.85 M, 1.9 M, 1.95 M, or 2 M). In certain embodiments, the concentration of nonbuffering salt in the wash solution is 1 M or greater. In particular embodiments, the nonbuffering salt in the wash solution is present at a concentration of 0.75 M or about 0.75 M, 1.0 M or about 1.0 M, or 1.25 M or about 1.25 M.

The pH of the wash solutions of the invention typically is greater than 8.0, although lower pHs are also suitable for use with the wash solution(s) of the invention. In a particular embodiment, the pH is greater than 8.0, preferably at least 8.1, more preferably at least 8.5 or 8.9. In one embodiment, the pH of the one or more wash solutions is in a range of 8.1-9.5. In another embodiment, the pH of the one or more wash solutions is in a range of 8.5-9.5. In another embodiment, the pH of the one or more wash solutions is about 9.0. In another embodiment, the pH of the one or more wash solutions is 9.0. Alternatively, depending on the protein of interest to be purified, a lower pH value can be used, for example a pH in a range of pH 5.0-8.0, or a pH of 7.5 or 7.0 or 6.5 or 5.0. Depending on the properties of the protein to be purified, the ordinarily skilled artisan can select an appropriate pH value for the wash solution. Accordingly, the wash solution(s) can contain one or more buffers for adjusting and/or maintaining the pH. Non-limiting examples of typical buffers that can be included in the wash solution(s) include Tris (tris(hydroxymethyl)methylamine), bis-Tris, bis-Tris propane, histidine, triethanolamine, diethanolamine, formate, acetate, MES (2-(N-morpholino)ethanesulfonic acid), phosphate, HEPES (4-2-hydroxyethyl-1-piperazineethanesulfonic acid), citrate, MOPS (3-(N-morpholino)propanesulfonic acid), TAPS (3-{[tris(hydroxy methyl)methyl]amino}propanesulfonic acid), Bicine (N,N-bis(2-hydroxyethyl)glycine), Tricine (N-tris(hydroxymethyl)methylglycine), TES (2-{[tris(hydroxymethyl)methyl]amino}ethanesulfonic acid), PIPES (piperazine-N,N'-bis(2-ethanesulfonic acid), cacodylate (dimethylarsinic acid) and SSC (saline sodium citrate).

The arginine and nonbuffering salt wash combination described herein preferably is applied in a single wash solution that contains both components. Alternatively, two wash solutions, one containing arginine or arginine derivative (preferably at high pH) and the other containing a nonbuffering salt can be used in tandem washes. Accordingly, in another embodiment of the washing method, the AC matrix is washed with two wash solutions, a first wash solution and a second wash solution, prior to elution of the protein of interest. In one embodiment, the first wash solution comprises arginine, or an arginine derivative, (preferably at a pH greater than 8.0) and the second wash solution comprises a nonbuffering salt. In another embodiment, the first wash solution comprises a nonbuffering salt and the second wash solution comprises arginine, or an arginine derivative, (preferably at a pH greater than 8.0). Examples of suitable arginine derivatives and nonbuffering salts, as well as preferred concentrations, concentration ranges and pH conditions for the wash solutions are as described above.

The washing method of the invention is effective in removing a variety of impurities, including high molecular weight (HMW) species and host cell proteins (HCPs). As described in detail in the Examples, the wash solutions of the invention are effective in reducing both HMW species and HCPs in the eluate, while achieving a high percent yield of the protein of interest in the eluate and a high concentration of the protein of interest in the eluate. For example, in various embodiments, use of the washing method described herein results in a percent yield of the protein of interest that is greater than 95%, more preferably greater than 96%, even more preferably greater than 97%. With respect to the reduction in HMW species in the eluate, which can be expressed as the % HMW in the eluate, in various embodiments use of the washing method described herein results in a % HMW in the eluate that is less than 10%, or less than 5%, or less than 2.0%, or less than 1% or less than 0.5%. With respect to the reduction in HCPs in the eluate, which can be expressed as the logarithmic reduction value (LRV), in various embodiments use of the washing method described herein results in an LRV for HCPs in the eluate that is at least 1.1, or at least 1.3, or at least 1.5, or at least 2.0, or at least 2.3, or at least 2.5, or at least 2.7.

Although the invention is described herein with respect to a washing step during affinity chromatography, it will be readily apparent to the ordinarily skilled artisan that additional steps are carried out both before and after the washing step to achieve purification of the protein of interest from the affinity chromatography matrix. For example, prior to the washing step, the methods of the invention can include an equilibration step, in which the affinity chromatography matrix is equilibrated with a loading buffer, and a loading or capture step, in which a biochemical mixture (e.g. cellular harvest) containing the protein of interest is applied to the AC matrix. Suitable conditions for the equilibration and loading buffers will vary depending upon the nature of the AC matrix and the protein of interest to be purified, and the ordinarily skilled artisan can readily determine such conditions using methods and information well established in the art. Non-limiting examples of equilibration and loading buffers for the purification of antibodies on Protein A columns are set forth in Examples 1 and 2. Additionally, after the washing step(s) as mentioned above, the methods of the invention can include one or more additional washings step(s) utilizing common wash solutions, and/or an elution step, in which an elution buffer is applied to the affinity chromatography matrix to elute the protein of interest from the matrix. Suitable conditions for the elation buffer will vary depending upon the nature of the AC matrix and the protein of interest to be purified, and the ordinarily skilled artisan can readily determine such conditions using methods and information well established in the art. Typically, elution of the protein of interest from the AC matrix is carried out at an acidic pH. N-limiting examples of an elution buffers for the purification of antibodies on Protein A columns are set forth in Examples 1 and 2.

In another aspect, the invention provides preferred methods for removing impurities from antibody-containing mixtures during Protein A purification of the antibody. Accordingly, the invention provides a method of producing a purified antibody, or antibody fragment, using a Protein A column, the method comprising a) loading a mixture comprising the antibody, or antibody fragment, onto the Protein A column;

b) washing the Protein A column with a wash solution comprising (i) Arginine-HCl at a concentration in a range of 0.05-2.0 M (more preferably in a range of 0.05-0.85 M, most preferably in a range of 0.1-0.5 M) and (ii) sodium chloride, at a concentration in a range of 0.1-2.0 M, wherein the wash solution removes impurities from the Protein A column; and c) elating the antibody, or antibody fragment, from the Protein A column.

Preferably, the wash solution is at a pH greater than 8.0. Preferred concentrations and concentration ranges for the Arginine-HCl are as described above. For example, in a preferred embodiment, the Arginine-HCl is at a concentration of about 0.25 M or at a concentration of 0.25 M. Preferred concentrations and concentration ranges for the sodium chloride are as described above. For example, in a preferred embodiment, the sodium chloride is at a concentration of about 1 M or at a concentration of 1 M. Preferred pHs and pH ranges also are as described above. For example, in one embodiment, the pH of the wash solution is in a range of 8.1-9.5. In another embodiment, the pH of the wash solution is 8.5 or greater. In another embodiment, the pH of the wash solution is 9.0.

The present invention is further illustrated by the following examples, which should not be construed as further limiting. The contents of all references, patents and published patent applications cited throughout this application are expressly incorporated herein by reference in their entirety.

EXAMPLES

Example 1

Comparison of Arginine/Nonbuffering Salt Wash Solution to Other Wash Solutions

In this example, the effectiveness of various wash solutions to remove impurities from an antibody-containing solution during affinity chromatography is compared. More specifically, three wash solutions are compared: one containing no arginine and no nonbuffering salt at pH 5.0, the second containing nonbuffering salt but no arginine at pH 7.0, and the third containing both nonbuffering salt and arginine at pH 9.0.

Clarified, mammalian cell culture supernatants containing between 1.5 and 2.5 g/L antibody are harvested by depth filtration and purified using an ALC column, in particular a Protein A column (GE Healthcare), according to the conditions described below in Table 1:

TABLE 1

Operating Conditions for Protein A Column

| Step | Buffer | CV** | Res. time * (min) |
|---|---|---|---|
| Equilibration | 20 mM NaH$_2$PO$_4$/Na$_2$HPO$_4$, pH 7.0 | 6 | 4 |
| Load | Cell-free harvest | q.s. | 4 |
| Wash 1 | Variable (See Table 2) | 3 | 4 |
| Wash 2 | 20 mM NaH$_2$PO$_4$/Na$_2$HPO$_4$, pH 7.0 | 3 | 4 |
| Elution | 20 mM Acetic acid | 4 | 4 |
| CIP | 0.1M NaOH | 3 | 4 |
| Storage | 20 mM Acetic acid/Sodium acetate, 2% Benzylalkohol, pH 5.1 | 4 | 4 |

* Res. Time = residence time;
** CV, columns volume

The equilibrated column is loaded with clarified harvest and is first washed with wash solution 1, described in Table 2 below, followed by a second wash with wash solution 2 (20 mM NaH$_2$PO$_4$/Na$_2$HPO$_4$, pH 7.0), and then eluted at low pH. The eluate is analyzed for its antibody concentration by analytical ALC, for HMW/LMW by analytical size exclusion chromatography (SEC) and for HCP content by enzyme-linked immunosorbent assay, developed on the same cell line. The various wash solutions compared for the first wash are shown below in Table 2:

TABLE 2

Variant Wash Solutions for First Wash

| Solution | Buffer | Abbreviation of buffer |
|---|---|---|
| 1 | 20 mM sodium acetate, 6 mM acetic acid pH 5.0 | W1-A5 |
| 2 | 20 nM NaH$_2$PO$_4$/Na$_2$HPO$_4$, 1000 mM NaCl, pH 7.0 | W2-N7 |
| 3 | 50 mM Tris, 250 mM Arginine-HCl, 1M NaCl, NaOH * pH 9.0 | W3-Arg/N9 |

* pH adjusted with 32% NaOH solution

The percent yields for the Protein A purification of four different monoclonal antibodies (mAb), using the three different wash solutions shown in Table 2, are shown below in Table 3.

TABLE 3

Percent Yields of Different Antibodies Using Various Wash Solutions

| | Wash Solution | | |
|---|---|---|---|
| Antibody | W1-A5 | W2-N7 | W3-Arg/N9 |
| mAb-Qg | 81.2 | 101.3 | 97.8 |
| mAb-By | 86.6 | 96.5 | 97.6 |
| mAb-Bp | 95.7 | 92.5 | 95.8 |
| mAb-Va | 96.5 | 97.9 | 98.6 |

Table 3 shows that washing with either W1-A5 (containing no nonbuffering salt or arginine, at pH 5.0) or W2-N7 (containing nonbuffering salt but no arginine, at pH 7.0) results in fluctuations in the amount of antibody recovered depending on the antibody being purified. More specifically, washing with W1-A5 results in yields fluctuating between 81 and 96% and washing with W2-N7 results in yields fluctuating between 92 and 101%. In contrast, washing with W3-Arg/N9, containing both nonbuffering salt and arginine, at pH 9.0, results in consistently high yields, above 96%, for all four antibodies being purified.

The eluate concentrations (in g/L), after the Protein A purification of the four different mAbs, using the three different wash solutions shown in Table 2, are shown below in Table 4.

TABLE 4

Eluate Concentration of Different Antibodies Using Various Wash Solutions

| | Wash Solution | | |
|---|---|---|---|
| Antibody | W1-A5 | W2-N7 | W3-Arg/N9 |
| mAb-Qg | 17.3 | 17.7 | 28.4 |
| mAb-By | 12.6 | 19.8 | 21.0 |
| mAb-Bp | 23.5 | 17.2 | 21.2 |
| mAb-Va | 15.1 | 14.3 | 16.4 |

Table 4 shows that the eluate concentration is also influenced by the wash buffer applied during ALC. For three of the four mAbs (mAbs Qg, By and Va), washing with W3-Arg/N9 results in higher eluate concentrations than washing with W1-A5 or W2-N7. The average eluate concentration for the four antibodies is lowest after the W1-A5 wash (17.1 g/L), followed by the W2-N7 wash (17.3 g/L) and highest after the wash with W3-Arg/N9 (21.7 g/L).

The reduction in host cell protein (HCP) in the eluates after the Protein A purification of the four different mAbs, using the three different wash solutions shown in Table 2, are shown below in Table 5. The reduction in HCP is expressed as the logarithmic reduction value (LRV) with respect to the values in the cellular harvest.

TABLE 5

Reduction in HCP in Eluate for Different Antibodies Using Various Wash Solutions

| Antibody | Wash Solution | | |
|---|---|---|---|
| | W1-A5 | W2-N7 | W3-Arg/N9 |
| mAb-Qg | 1.50 | 1.64 | 2.75 |
| mAb-By | 1.40 | 1.68 | 2.55 |
| mAb-Bp | 1.77 | 1.88 | 2.53 |
| mAb-Va | 0.94 | 0.99 | 1.33 |

With respect to the impurity removal, based on the data in Table 5 a clear order can be established between the three wash buffers. The lowest HCP reduction is obtained with the low pH wash W1-A5, followed by the wash with salt wash W2-N7 and the highest removal factor is obtained with the arginine-NaCl combination buffer at pH 9.0 (W3-Arg/N9). Expressed in logarithmic order of removal, an average of 1.4 logs is obtained after washing with W1-A5, 1.55 logs with W2-N7 and the highest removal of 2.2 logs is achieved with W3-Arg/N9.

The level of high molecular weight (HMW) species in the eluates after the Protein A purification of the four different mAbs, using the three different wash solutions shown in Table 2, are shown below in Table 6. The level of BMW species in the eluates is expressed as a percentage (%) of the total protein in the eluates.

TABLE 6

Level of HMW Species in Eluate for Different Antibodies Using Various Wash Solutions

| Antibody | Wash Solution | | |
|---|---|---|---|
| | W1-A5 | W2-N7 | W3-Arg/N9 |
| mAb-Qg | 4.7 | 3.8 | 0.8 |
| mAb-By | 2.1 | 0.7 | 0.4 |
| mAb-Bp | 10.4 | 10 | 9.8 |
| mAb-Va | 4.1 | 2.9 | 1.6 |

Table 6 shows that the level of HMW species is very heterogeneous for the 4 different mAbs and the removal of HMWs is mAb-dependent. Overall, the W1-A5 wash solution is the least effective washing solution. Better results are obtained with the W2-N7 wash solution and the lowest HMW values in the ALC eluate are consistently found with the W3-Arg/N9 wash solution. Three mAbs (mAbs Qg, By and Va) respond with a 2.6 to 5.9-fold reduction in HMWs comparing the W1-A5 wash versus the W3-Arg/N9 wash, whereas mAb-Bp only showed a marginal reduction.

A summary of the findings for the experiments summarized in Tables 3-6 above is shown below in Table 7. The shaded row represents the composition of the harvest.

TABLE 7

Comparison of Three ALC Wash Solutions for Four mAbs

| mAb | Wash buffer | Yield [%] | Conc. [g/L] | HCP [ppm] | HCP [LRV] | HMW [%] |
|---|---|---|---|---|---|---|
| Va | Harvest | NA | 1.53 | 337739 | NA | NA |
| Va | Acetate pH 5.0 | 96.5 | 15.1 | 38620 | 0.94 | 4.1 |
| Va | NaCl pH 7.0 | 97.9 | 14.3 | 34522 | 0.99 | 2.9 |
| Va | Arg/NaCl pH 9.0 | 98.6 | 16.4 | 15618 | 1.33 | 1.6 |
| Qg | Harvest | NA | 1.65 | 645236 | NA | NA |
| Qg | Acetate pH 5.0 | 81.2 | 17.3 | 20393 | 1.500237 | 4.7 |
| Qg | NaCl pH 7.0 | 101.3 | 17.7 | 14673 | 1.6432 | 3.8 |
| Qg | Arg/NaCl pH 9.0 | 97.8 | 28.4 | 1150 | 2.749021 | 0.8 |
| By | Harvest | NA | 2.29 | 528326 | NA | NA |
| By | Acetate pH 5.0 | 86.6 | 12.6 | 20955 | 1.401614 | 2.1 |
| By | NaCl pH 7.0 | 96.5 | 19.8 | 11111 | 1.677149 | 0.7 |
| By | Arg/NaCl pH 9.0 | 97.6 | 21.0 | 3738 | 2.150263 | 0.4 |
| Bp | Harvest | NA | 1.69 | 523191 | NA | NA |
| Bp | Acetate pH 5.0 | 95.7 | 23.5 | 8830 | 1.7727 | 10.4 |
| Bp | NaCl pH 7.0 | 92.5 | 17.2 | 6845 | 1.883287 | 10 |
| Bp | Arg/NaCl pH 9.0 | 95.8 | 21.2 | 1543 | 2.530294 | 9.8 |

Conc. = eluate concentration;

HCP = host cell proten;

HMW = high molecular weight species;

LRV = log reduction value;

NA = not applicable.

Example 2

Comparison of Various Arginine/Salt Wash Solutions

In this example, the effectiveness of additional wash solutions, containing different amounts of nonbuffering salt and/or arginine at different pH values, to remove impurities during affinity liquid chromatography (ALC) is compared. The chromatography conditions used in this Example are as set forth in Table 8 below.

TABLE 8

Operating Conditions for Protein A Column

| Step | Buffer | CV ** | Res. time * (min) |
|---|---|---|---|
| Equilibration 1 | 20 mM $NaH_2PO_4/Na_2HPO_4$, pH 7.0 | 3 | 4 |
| Equilibration 2 | Identical to wash buffer 1 | 3 | 4 |
| Load | Cell-free harvest | q.s. | 4 |
| Wash 1 | Variable (See Table 9) | 6 | 4 |
| Wash 2 | 20 mM $NaH_2PO_4/Na_2HPO_4$, pH 7.0 | 3 | 4 |
| Elution | 50 mM Acetic acid | 5 | 4 |
| CIP | 0.1M NaOH | 3 | 4 |
| Storage | 20 mM Acetic acid/Sodium acetate, 2% Benzylalkohol, pH 5.1 | 5 | 4 |

* Res. Time = residence time;
** CV, column volume

The wash solutions compared in this Example are set forth below in Table 9:

TABLE 9

Additional Variant Wash Solutions for First Wash

| Solution | Buffer | Abbreviation of buffer |
|---|---|---|
| 1 | 20 mM $NaH_2PO_4/Na_2HPO_4$, 1000 mM NaCl, pH 7.0 | W2-N7 |
| 2 | 20 mM $NaH_2PO_4/Na_2HPO_4$, 150 mM NaCl, pH 7.0 | W4-0.15M N7 |
| 3 | 250 mM Arginine-HCl, ~18 * mM Tris-HCl, pH 8.0 | W5-Arg8 |
| 4 | ~18 * mM Tris-HCl, 250 mM Arginine-HCl, 1M NaCl, pH 8.0 | W6-Arg/N8 |

* The exact concentration was not measured (1M Tris base [(hydroxymethyl) aminomethane] was used to adjust the pH)

The four wash solutions shown in Table 9 allow direct comparison of a low nonbuffering salt wash solution (W4-0.15M N7, containing 150 mM NaCl) to a high nonbuffering salt wash solution (W2-N7, containing 1M NaCl), as well as comparison of a wash solution containing arginine alone at pH 8.0 (W5-Arg8) to a wash solution containing the combination of nonbuffering salt with arginine at basic pH (W6-Arg/N8).

The percent yield, percent HMW species in eluate, and reduction in HCP (expressed as LRV) for purification of mAb-By, using the four different wash solutions shown in Table 9, as well as the combination of the arginine alone wash (W5-Arg8) with the high salt alone wash (W2-N7), are shown below in Table 10.

TABLE 10

Purification Values for mAb-By Using Various Wash Solutions

| Purification Value | Wash Solution | | | | |
|---|---|---|---|---|---|
| | W4-0.15M N7 | W2-N7 LW * | W5-Arg8 | W5-Arg8, W2-N7 | W6-Arg/N8 |
| Yield (%) | 98.4 | 100 | 99.3 | 97.4 | 97.9 |
| HMW (%) | 1.6 | 0.9 | 0.5 | 0.3 | 0.3 |
| HCP (LRV) | 1.81 | 2.19 | 2.35 | 2.57 | 2.7 |

* LW = washing was performed for 12 column volumes instead of 6.

Table 10 shows that the percent yield of the antibody remains above 97% for all washing conditions. Moreover, the most efficient wash solutions for removal of impurities, both HMWs and HCPs, are the wash solution that contains both arginine and high nonbuffering salt at basic pH (W6-Arg/N8) or the combined use of the wash solutions that contain arginine at basic pH (W5-Arg8) and high nonbuffering salt (W2-N7).

Washing with a rather physiological wash solution, W4-0.15M N7, reduces the HCPs by 64-fold (1.81 logs) as compared to the starting material that is loaded onto the column. In contrast, washing with a nonbuffering salt-arginine combination at pH 8 (W6-Arg/N8) results in a reduction by 498-fold (2.7 logs).

The reduction of HMWs follows a similar trend. Washing with the wash solution containing 20 mM sodium phosphate, 150 mM NaCl, pH 7.0 (W4-0.15M N7) results in 1.6% HMWs in the eluate, whereas washing with the nonbuffering salt-arginine combination (W6-Arg/N8) reduces this value by more than 5-fold.

Example 3

Comparison of Basic pH to Physiological pH in Wash Solutions

In this example, an analysis of the pH as a parameter of the wash solutions on the removal of HCPs and HMWs is conducted and shows the superiority of basic pH conditions. Affinity liquid chromatography (ALC) using the conditions set forth in Table 8 in Example 2, is performed on a cellular harvest of mAb-Va, with slightly different levels of HMW and HCPs.

The wash solutions compared in this Example are set forth below in Table 11:

TABLE 11

Wash Solutions with Varying pH Values for First Wash (on mAb-Va)

| Solution | Buffer | Abbreviation of buffer |
|---|---|---|
| 1 | 20 mM $NaH_2PO_4/Na_2HPO_4$, 1000 mM NaCl, pH 7.0 | W2-N7 |
| 2 | 13.2 mM $Na_2HPO_4$, 250 mM Arginine HCl, 1M NaCl, pH 7.0 | W6-Arg/N7 |
| 3 | ~289 mM * Tris, 250 mM Arginine-HCl, 1M NaCl, pH 8.9 | W3b-Arg/N8.9 |

* No NaOH was used for pH adjustment

The percent yield, percent HMW species in eluate, and reduction in HCP (expressed as LRV) for purification of mAb-Va, using the three different wash solutions shown in Table 11, are shown below in Table 12.

TABLE 12

Comparison of Physiological pH with Basic
pH on Purification Values for mAb-Va

| Purification | Wash Solution | | |
|---|---|---|---|
| Value | W2-N7 | W6-Arg/N7 | W3b-Arg/N8.9 |
| Yield (%) | 100.5 | 99.4 | 99 |
| HMW (%) | 2.4 | 3.6 | 1.4 |
| HCP (LRV) | 0.87 | 1.48 | 1.61 |

The high nonbuffering salt alone wash solution, W2-N7, serves as a baseline control wash to establish the HCP/HMW removal ability of the arginine/nonbuffering salt combination at approximately physiological pH 7.0 (wash solution W6-Arg/N7) and at basic pH 8.9 (wash solution W3b-Arg/N8.9). A small but noticeable reduction in HMW levels from 1.6 to 1.4% is observed at the higher pH (pH 8.9) as compared to the lower pH (pH 7.0). More evident is the effect on the HCP removal. Here, the lower pH wash (pH 7.0) reduces the HCPs by 1.48 logs, whereas the high pH wash (pH 8.9) reduces the value by 1.61 logs, underlining the superiority of the high pH wash in impurity removal capacity.

Example 4

Comparison of Arginine/Salt Wash Solution to Other Wash Solutions

In this example, other wash solutions, containing Tween 80, amino acids other than arginine or high concentrations of Tris, are compared to the arginine/nonbuffering salt wash solutions. In this example, an analysis of the pH as a parameter of the wash solutions on the removal of HCPs and HMWs is conducted and shows the superiority of basic pH conditions. Affinity liquid chromatography (ALC) using the conditions set forth in Table 1 in Example 1, is performed on a cellular harvest of mAb-Va, with slightly different levels of HMW and HCPs.

The wash solutions compared in this Example are set forth below in Table 13:

TABLE 13

Wash Solutions with Varying Components for First Wash

| Solution | Buffer | Abbreviation of buffer |
|---|---|---|
| 1 | 20 mM $NaH_2PO_4/Na_2HPO_4$, 1000 mM NaCl, pH 7.0 | W2-N7 |
| 2 | 20 mM $NaH_2PO_4/Na_2HPO_4$, 1000 mM NaCl, pH 7.0 | W2-N7 LW* |
| 3 | 20 mM $NaH_2PO_4/Na_2HPO_4$, 1000 mM NaCl, 0.1% (w/v) Tween80, pH 7.0 | W7-N7-T80 |
| 4 | 20 mM $NaH_2PO_4/Na_2HPO_4$, 1000 mM NaCl, 0.1M Glycine, Tris** | W8-N7-0.1 M G |
| 5 | 500 mM Tris, pH 8.9 | W9-0.5 M Tris 8.9 LW* |
| 6 | 289 mM Tris, 250 mM Arginine-HCl, 1M NaCl, pH 8.9 | W3b-Arg/N8.9 |

*LW = washing was performed for 12 column volumes instead of 6.
**pH adjusted with 1M stock solution, conc. not measured.

The percent yield, percent HMW species in eluate, and reduction in HCP (expressed as LRV) for purification of mAb-Va, using the six different wash solutions shown in Table 13, are shown below in Table 14.

TABLE 14

Comparison of Wash Solution Components
on Purification Values for mAba-Va

| Purification Value | Wash Solution | | | | | |
|---|---|---|---|---|---|---|
| | W2-N7 | W2-N7 LW * | W7-N7-T80 | W8-N7-0.1M G | W9-0.5M Tris 8.9 LW * | W3b-Arg/N8.9 |
| Yield (%) | 100.5 | 100.9 | 99 | 98.7 | 98.1 | 99 |
| HMW (%) | 2.4 | 2.3 | 2.5 | 3.1 | 3 | 1.4 |
| HCP (LRV) | 0.87 | 1.42 | 1.34 | 1.24 | 1.07 | 1.61 |

* LW = washing was performed for 12 column volumes instead of 6.

Table 14 shows that the arginine/nonbuffering salt wash solution at high pH (W3b-Arg/N8.9) is the most efficient wash solution in removing both HMWs and HCPs, as compared to other wash solutions containing high nonbuffering salt alone (W2-N7), Tween 80 (W7-N-7-T80), other amino acids such as glycine (W8-N7-0.1 M G) or high concentrations of Tris (W9-0.5 M Tris 8.9 LW).

Example 5

Comparison of Arginine/Nonbuffering Salt Wash Solution at High pH to Salt Alone at Low and High pH In this example, the effectiveness of the arginine/nonbuffering salt wash solution at a high pH is compared to a nonbuffering salt solution at high and low pHs. Specifically, the following conditions are evaluated and compared: (1) nonbuffering salt wash solution at a low pH (i.e., 7.0), 2) nonbuffering salt wash solution at a high pH (i.e., 9.0), and (3) nonbuffering salt wash solution in combination with arginine at a high pH (i.e., 9.0). Additionally, the effect of arginine on the removal of HMWs, LMWs and HCPs is analyzed, and shows that using the nonbuffering salt solution in combination with arginine at basic pH conditions is particularly effective and advantageous. The wash solutions compared in this Example are set forth below in Table 15:

TABLE 15

Wash Solutions with Varying Components for First Wash

| Solution | Buffer | Abbreviation of buffer |
|---|---|---|
| 1 | 20 mM $NaH_2PO_4/Na_2HPO_4$, 1000 mM NaCl, pH 7.0 | W2-N7 |
| 2 | 20 mM $NaH_2PO_4/Na_2HPO_4$, 1000 mM NaCl, NaOH, pH 9.0 * | W10-N9 |
| 3 | 50 mM Tris, 250 mM Arginine-HCl, 1M NaCl, NaOH, pH 9.0 * | W3-Arg/N9 |

* pH adjusted to 9.0 with 32% stock solution of NaOH.

Affinity liquid chromatography (ALC) using the conditions set forth in Table 1 in Example 1, is performed on a cellular harvest of mAb-By, using different levels of HMWs and HCPs with minimal variations, as detailed below in Table 16.

TABLE 16

Operating Conditions for Protein A Column

| Step | Buffer | CV | Res. Time** (min) | Comment |
|---|---|---|---|---|
| Equilibration | 20 mM NaH$_2$—/Na$_2$H—PO$_4$, pH 7.0 | 5/6* | 4 | |
| Load | Cell-free harvest | | 4 | 36 mg/ml Resin |
| Wash 1 | See Table 15 | 6 | 4 | |
| Wash 2 | EQ | 3 | 4 | |
| Elution | 20 mM Acetic acid, pH tq*** | 5/4* | 4 | 100-100 mAU at 280 nm |
| CIP | 0.1M NaOH | 4 | 4 | |
| Storage | 20 nM Na-acetate, 2% Benzylalkohol, pH 5.1 | 5/4* | 4 | |

*for the run with wash solution W3-Arg/N9, 6 CV were used for equilibration and 4 CV were used for elution and storage.
**Res. Time = residence time.
***tq = tel quel (as is).

The parameters of (1) SEC-derived antibody concentration (g/L), (2) percent HMW and LMW species, (3) HCP level expressed, in ng/mg monoclonal antibody and, (4) ALC-derived percent yield in the ALC eluate were measured for purification of mAb-By, using the three different wash solutions shown in Table 15. The results are shown below in Table 17.

TABLE 17

Comparison of Wash Solution Components on Purification Values for mAb-By

| Wash Solution | Conc. (g/L) | HMW (%) | LMW (%) | HCP (mg/mg MAb) | Yield (%) |
|---|---|---|---|---|---|
| Starting material | 2.32 | NA | NA | 370962 | (100) |
| W2-N7 | 20.00/19.84* | 1.3/0.9* | 0.4/0.4* | 9315/6783* | 100.8/ND* |
| W10-N9 | 20.28/20.10* | 1.2/3.0* | 0.5/0.5* | 8984/7884* | 101.9/ND* |
| W3-Arg/N9 | 20.55 | 0.8 | 0.1 | 211.0 | 100.3/ND* |

*the second value corresponds to a second measurement after filtration through 0.2 μm filter.

Specifically, Table 17 shows that the arginine/nonbuffering salt wash solution at high pH of 9.0 (W3-Arg/N9) is the most efficient wash solution for removing HMWs, LMWs and HCPs, as compared to other wash solutions containing nonbuffering salt alone (W2-N7 and W10-N9), independent of their pH. In particular, washing with the arginine/non-buffering salt wash solution at a pH of 9.0 reduced the HCP's by at least 3-fold and the LMWs by at least 4-fold, as compared to washing with the nonbuffering salt alone at a pH of 7 (W2-N7) or a pH of 9 (W10-N9).

Example 6

Comparison of Ranges of Arginine and NaCl Concentrations and pH for the Arginine/Salt Wash Solution In this example, additional arginine and non-buffering salt concentrations and pH washing conditions are investigated to determine their effective on removing impurities during affinity liquid chromatography (ALC). The wash solutions compared in this Example are set forth below in Table 18:

TABLE 18

Wash Solutions with Varying Components for First Wash

| Solution | Buffer | Abbreviation of buffer |
|---|---|---|
| 1 | 0.75M NaCl, 250 mM L-Arginine/Tris pH 8.5 * | W11-Arg/N8.5 |
| 2 | 1.25M NaCl, 250 mM L-Arginine/Tris, pH 9.5 * | W12-Arg/N9.5 |
| 3 | 50 mM Tris, 500 mM Arginine-HCl, 1M NaCl, NaOH, pH 9.0 * | W13-Arg/N9 |
| 4 | 10 mM Tris, 100 mM Arginine-HCl, 1M NaCl, NaOH, pH 9.0 * | W14-Arg/N9 ** |

* pH adjusted with 8M NaOH;
** buffer obtained through 5-fold dilution of W13-Arg/N9 and pH adjustment to 9.0 with 8M NaOH.

ALC is performed on a cellular harvest of mAb-By (under the conditions set forth in Table 1 in Example 1), using slightly different levels of HMW and HCPs with minimal variations, as detailed below in Table 19.

TABLE 19

Operating Conditions for Protein A Column (at 4 min res. time)[+]

| Step | Buffer | CV | Comment |
|---|---|---|---|
| Equilibration | 20 mM NaH2—/Na2H—PO4, pH 7.0 | 6 | |
| Load | Cell-free harvest | | 38 mg/ml resin |
| Wash 1 | See Table 18 | 4.5[*]/7.5[]/6[**] | |
| Wash 2 | EQ | 3 | |
| Elution | 50 mM acetic acid, pH 3.5[*]/[]/[*] or 50 mM acetic acid, pH 3.8[**]/[*] | 4/6[**] | 500-500 mAU/cm at 280 nm |
| CIP | 0.1M NaOH | 4/3[****] | Up flow |
| Storage | 20 mM Na-acetate, 2% Benzylalkohol, pH 5.1 | 4 | Up flow |

[*]for run with wash solution W11-Arg/N8.5;
[**]for run with wash solution W12-Arg/N9.5;
[***]pH adjusted with 1M Tris;
[****]for run with wash solution W13-Arg/N9 and W14-Arg/N9;
[*****]pH adjusted with 8M NaOH.
[+]Res. Time = residence time.

The parameters of (1) SEC-derived antibody concentration (g/L), (2) percent HMW and LMW species (%), (3) HCP level expressed in ng/mg monoclonal antibody, and (4) ALC-derived percent yield in the ALC eluate were measured after purification of mAb-By using either of the two different wash solutions shown in Table 18. These results are shown below in Table 20.

TABLE 20

Efficiency of the wash buffer at different NaCl concentrations and pH levels for the purification of mAb-By (two different starting materials)

| Applied wash solution | Concentration (mg/ml) (SEC) | HMW (%) | LMW (%) | HCP (ng/mg) | Yield (%) (ALC) |
|---|---|---|---|---|---|
| Starting material | 2.6 | NA | NA | 602398 | (100) |
| W12-Arg/N9.5 | 27.35 | 2.1 | 0.3 | 4637 | 100.4 |
| W11-Arg/N8.5 | 22.42 | 2.1 | 0.5 | 9922 | 100.2 |
| Starting material | 2.91 | NA | NA | 311761 | (100) |
| W13-Arg/N9 | 16.15 | 1.7 | 0.1 | 1367 | 98.7 |
| W14-Arg/N9 | 16.31 | 1.7 | 0.1 | 3405 | 95.9 |

The data shown in Table 20 underscores the efficacy of the arginine/nonbuffering salt wash solution at high pH, for use in for affinity liquid chromatography. Washing with (1) arginine and a lower concentration of nonbuffering salt (0.75 M NaCl) at a pH of 8.5, (2) arginine and a higher concentration of nonbuffering salt (1.25 M NaCl) at a pH of 9.5 or (3) either low (e.g., 100 mM) or high (e.g., 500 mM) concentrations of arginine, results in a strong reduction of HCPs (in average >2 logs reduction), without compromising the yield.

What is claimed is:

1. A method of producing a purified antibody, antibody fragment, or Fc fusion protein using an affinity chromatography (AC) matrix to which the antibody, antibody fragment, or Fc fusion protein is bound, the method comprising:
   (a) loading a mixture comprising the antibody, antibody fragment, or Fc fusion protein onto the AC matrix; and
   (b) washing the AC matrix with one or more wash solutions comprising arginine and a halogen salt selected from the group consisting of sodium chloride (NaCl), magnesium chloride ($MgCl_2$) and potassium chloride (KCl), wherein the pH of the one or more wash solutions is greater than 8.0, prior to elution of the antibody, antibody fragment, or Fc fusion protein from the AC matrix.

2. The method of claim 1, wherein the arginine is at a concentration of or about 0.25 M.

3. The method of claim 1, wherein the arginine is arginine-HCl.

4. The method of claim 1, wherein the halogen salt is at concentration of or about 1 M.

5. The method of claim 4, wherein the halogen salt is sodium chloride (NaCl).

6. The method of claim 1, wherein the pH of the wash solution is in a range of about 8.5-9.5.

7. The method of claim 6, wherein the pH of the wash solution is 9.0.

* * * * *